United States Patent [19]

Namikawa

[11] Patent Number: 4,852,132
[45] Date of Patent: Jul. 25, 1989

[54] METHOD OF COLLECTING DATA FOR X-RAY TOMOGRAPH

[75] Inventor: Jiro Namikawa, Tokyo, Japan

[73] Assignee: Yokogawa Medical Systems, Tokyo, Japan

[21] Appl. No.: 50,300

[22] PCT Filed: Aug. 29, 1985

[86] PCT No.: PCT/JP86/00442
§ 371 Date: Apr. 21, 1987
§ 102(e) Date: Apr. 21, 1987

[87] PCT Pub. No.: WO87/01268
PCT Pub. Date: Dec. 3, 1987

[30] Foreign Application Priority Data

Aug. 30, 1985 [JP] Japan .................. 60-191202

[51] Int. Cl.$^4$ ........................... G01N 21/34
[52] U.S. Cl. .......................... 378/19; 378/901
[58] Field of Search .......... 378/4, 19, 14, 901, 378/15, 146; 364/414

[56] References Cited

U.S. PATENT DOCUMENTS

| 4,075,490 | 2/1978 | Kowalski | 378/901 |
| 4,168,435 | 9/1979 | Duinker | 364/414 |
| 4,206,359 | 6/1980 | Hounsfield | 364/414 |
| 4,266,136 | 5/1981 | Duinker | 364/414 |
| 4,682,290 | 7/1987 | Tan et al. | 378/901 |
| 4,736,396 | 4/1988 | Boyd et al. | 378/4 |

FOREIGN PATENT DOCUMENTS 59-77836  5/1984 Japan .
59-19260 11/1985 Japan .

Primary Examiner—Carolyn E. Fields
Assistant Examiner—Joseph A. Hynds
Attorney, Agent, or Firm—Moonray Kojima

[57] ABSTRACT

The present invention which relates to a method of collecting data which enables exact opposing view data to be obtained as the real data with respect to data on any channel in an X-ray tomograph which uses fan beam X-rays is characterized in that the timing for collecting the output data of each detection channel is so selected that the relationship in which a pair of items of data based on a pair of X-ray beams which pass a substantially common route formed in a target in the opposite directions to each other are detected by a pair of channels which are situated at substantially symmetrical positions with respect to the center of an X-ray detector may be established with respect to all channels.

3 Claims, 4 Drawing Sheets

METHOD OF COLLECTING DATA FOR X-RAY TOMOGRAPH

DESCRIPTION

1. Technical Field

The present invention relates to a method of collecting data for an X-ray tomograph which uses continuous X-rays in the shape of fan beams.

2. Background Art

In a conventional X-ray tomograph, an which projects X-rays in the shape of fan beams and a multi-channel X-ray detector which opposes the X-ray source with an object to be examined (hereinunder referred to as "target") interposed therebetween are rotated around the target, so as to project the X-rays in the shape of fan beams along the section of the target, and the data which indicate the distribution of the transmission intensity of the X-rays in a plurality of directions in the section are measured, and the tomogram of the target is reconstructed on the basis of the data. In such a tomograph, the plurality of directions (hereinunder referred to as "view directions") in which the X-ray transmission data are collected are set at the directions obtained by dividing the trajectory of the rotation of the X-ray source and the X-ray detector around the target by an equal angle. These directions are determined by the timing of irradiation when the X-ray is a pulse X-ray, and by the timing for collection of X-ray transmission data when the X-ray is continuous X-rays.

The reconstruction of the tomogram of the target is carried out on the basis of the respective multi-channel data which have been collected in accordance with a predetermined number of views. The collected data are arranged in correspondence with the fan beam X-rays. The tomogram of the target may be reconstructed either directly from this arrangement of data, or after the arrangement is converted into the data arrangement which corresponds to parallel beam X-rays.

In order to enhance the resolution of the reconstructed image, the X-ray detector is sometimes disposed so that the central channel thereof is deviated from the X-ray which passes the center of rotation by ¼ (such a detector will hereinunder be referred to as "offset detector"), and the data on the symmetrical channels of the right half and the left half of the X-ray detector, which have been obtained at angles at which the view directions are substantially opposite, (hereinunder these data will be referred to as "opposing view data") are combined for reconstruction.

The opposing view data are also utilized for positively utilizing the duplexity of the data eve in an X-ray detector which does not adopt the offset arrangement.

In such a conventional X-ray tomograph, since the X-ray transmission data obtained are the data arranged in correspondence with the fan beam X-rays, the exact opposing view data are not always obtained with respect to all channels, so that utilization of opposing view data becomes incomplete.

DISCLOSURE OF THE INVENTION

Accordingly, it is an object of the present invention to provide a method of collecting data which enables exact opposing view data to be obtained with respect to the data on any channel in an X-ray tomograph which uses fan beam X-rays.

The present invention is characterized in that the timing for collecting the output data of each detection channel is so selected that the relationship in which a pair of items of data based on a pair of X-ray beams which pass a substantially common route formed in a target in the opposite directions to each other are detected by a pair of channels which are situated at substantially symmetrical positions with respect to the center of an X-ray detector may be established with respect to all channels.

BEST MODE OF CARRYING OUT THE INVENTION

Figure 1:
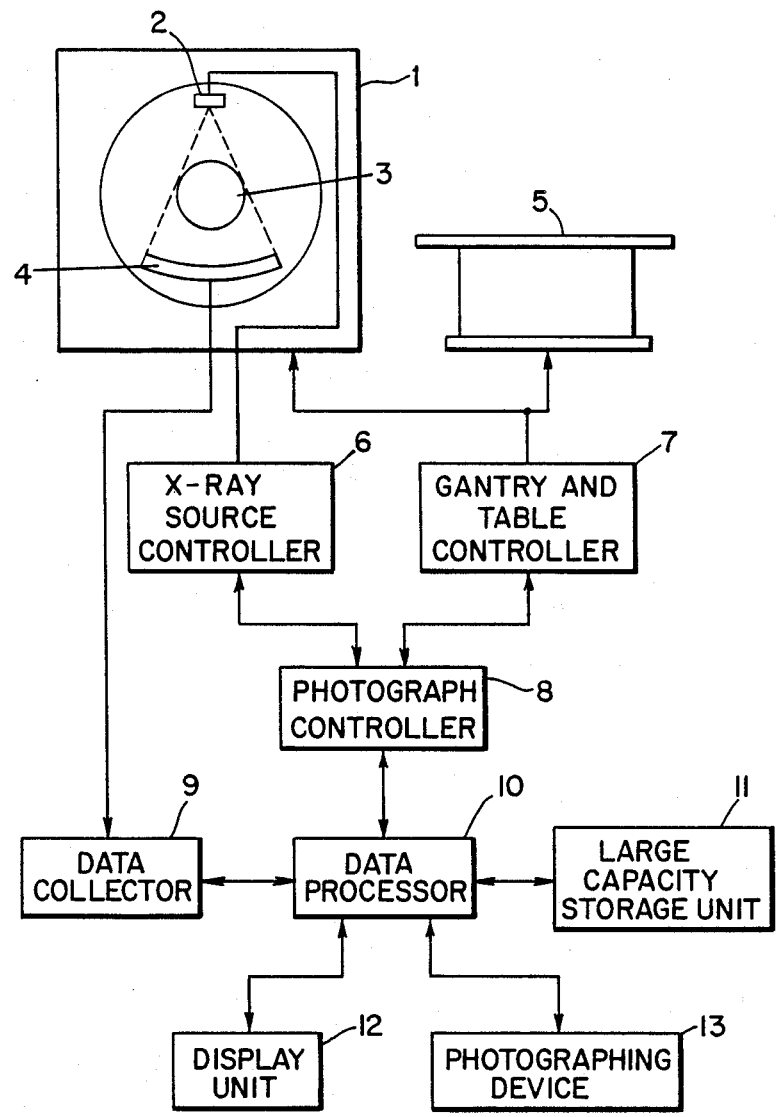
FIG. 1 is a schematic view of the structure of an embodiment of the present invention.

FIG. 1 is a schematic view of the structure of an embodiment of an X-ray tomograph according to the present invention. In FIG. 1, on a gantry 1 an X-ray source 2 and a multi-channel X-ray detector 4 are disposed in such a manner as to be opposed to each other with a predetermined positional relationship, and continuous X-rays in the shape of fan beams are projected from the X-ray source 2 to the X-ray detector 4. The continuous X-rays may contain a ripple. A target 3 mounted on a table 5 is fed to a space between the X-ray source 2 and the X-ray detector 4. The X-ray source 2 is controlled by an X-ray source controller 6. The gantry 1 is controlled by a gantry and table controller 7 and rotates around the target 3 while maintaining the relative positional relationship between the X-ray source 2 and the X-ray detector 4. The table 5 is controlled by the gantry and table controller 7, and positions the target 3 with respect to the gantry 1. The X-ray source controller 6 and the gantry and table controller 7 are controlled by a photograph controller 8.

The X-ray transmission data on a multiplicity of channels detected by the X-ray detector 4 are collected by a data collector 9 by a method which will be explained in detail later, and are converted into digital data to be supplied to a data processor 10.

The data processor 10 processes the supplied data to reconstruct the tomogram of the target 3, stores the reconstructed image in a large-capacity storage unit 11, at the same time displays it on a display unit 12, and makes the tomogram to be photographed by a photographing device 13, if necessary. The data processor 10 controls the photograph controller 8.

Such an apparatus of the embodiment of the present invention has the structure and the function which are substantially common to a known X-ray tomograph except for the X-ray detector 4 and the data collector 9.

The function of the data collector 9 which is characteristic of the embodiment of the present invention will now be explained. Preliminary subjects will first be explained.

Figure 2:
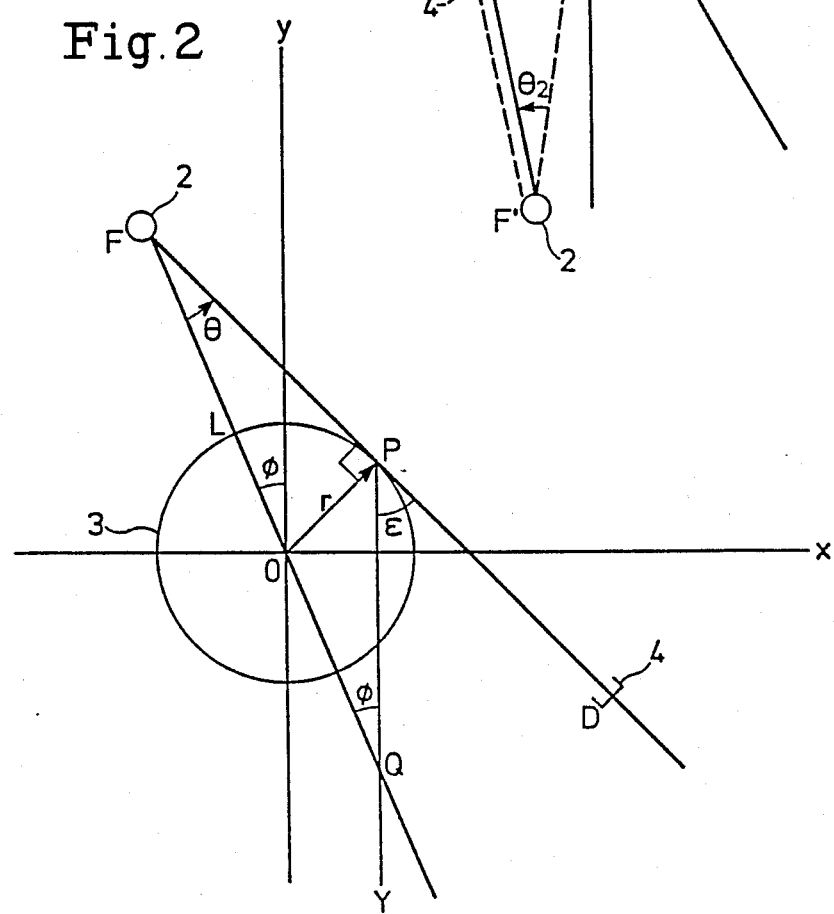

FIG. 2 shows a geometric relationship between the X-ray source 2 and the X-ray detector 4 in a certain view. In FIG. 2, the rotational position of the gantry is shown by the position of the X-ray source 2. That is, the gantry has rotated from the reference direction O→Y which is provisionally set, counterclockwise around the center O by the angle $\phi$, so that the view angle is $\phi$, and the X-ray beam which has started from the focal point F distant from the center O by L has passed. the point P of the target 3 which is r distant from the center O, and enters one channel D of the X-ray detector 4. The angle of the channel D seen from the focal point F is $\theta$ with F→O as the reference. The sign of the angle $\theta$ is determined to be positive counterclockwise.

A half-line Y which is parallel to the y-axis is drawn from the point P, and if the angle between the half-line Y and the direction F→P of the X-ray beam is assumed to be $\epsilon$, the following relationship holds:

$$r = L \sin \theta$$

$$\epsilon = \phi + \theta \qquad (1)$$

In the formula (1), r represents the position of the channel D and $\epsilon$ the angle of the X-ray beam which enters the channel D.

Figure 3:
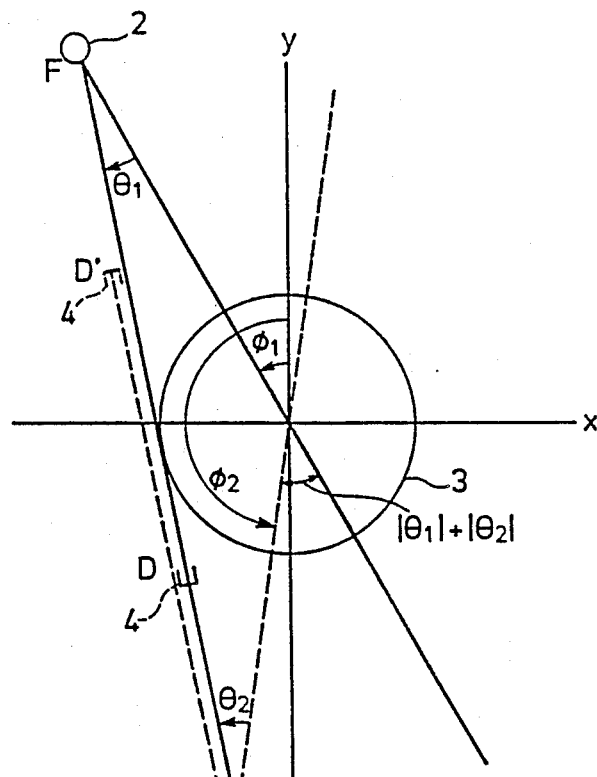
FIGS. 2, 3 and 6 show geometrical relationships among the X-ray source, the X-ray detector and the target in the embodiment of the present invention.

A similar geometrical relationship is shown in FIG. 3, in which the channel has a negative $\theta$. In FIG. 3, the X-ray beam is projected to the channel D having the angle $\theta 1$ ($<0$) at the view angle of $\phi 1$ to obtain X-ray transmission data on the target 3. Since the same data on the target 3 is obtained by the X-ray which passes the same portion of the target in the opposite direction, it is possible to obtain the same data by the channel D' which has the positive angle $\theta 2$ the absolute value of which is equal to $\theta 1$ at the view angle of $\phi 2$. If the relationship of the formula (1) is applied to this state, the following relationship holds:

$$r = L \sin \theta 2$$

$$\epsilon = \phi 2 + \theta 2$$

Since $\theta 2 = -\theta 1$ $$\phi 2 = \phi 1 + \pi - (\theta 2 - \theta 1),$$

the following formula holds:

$$r = -L \sin \Theta 1$$

$$\epsilon = \phi 1 + \theta 1 + \pi \qquad (2)$$

Figure 4:
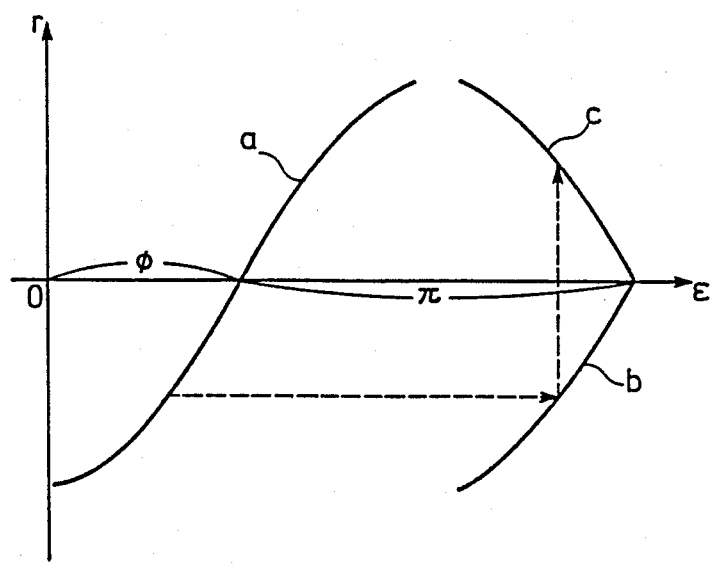
FIGS. 4, 5 and 7 show the characteristics of the arrangement of channel data of the X-ray detector in the embodiment of the present invention.

The formula (2) shows that the data on a channel on the negative $\theta$ side can be represented by the data on a channel on the positive $\theta$ side. This is shown in FIG. 4. FIG. 4 shows the position of each channel at the view angle of $\phi$ by a curve a on the plane $\epsilon-r$. The upper half of the curve a shows the position of a channel having a positive $\theta$, while the lower half of the curve a shows the position of a channel having a negative $\theta$. $\epsilon$ obtained from the formula (2) indicates that the portion of the curve in which $\theta$ is negative is moved parallel by $\pi$, and r in the formula (2) indicates that the sign of the portion of the curve in which $\theta$ is negative is reversed. If this is executed in FIG. 4, a curve c is obtained. That is, the portion of the curve a in which $\theta$ is negative can be represented by the curve c in which $\theta$ is in the positive range. The curves a and c are parts of one sine curve.

Since the above-described relationship holds with respect to all views, the position of the channels in all views can be represented only in the positive range of r on the plane $\epsilon-r$.

Figure 5:
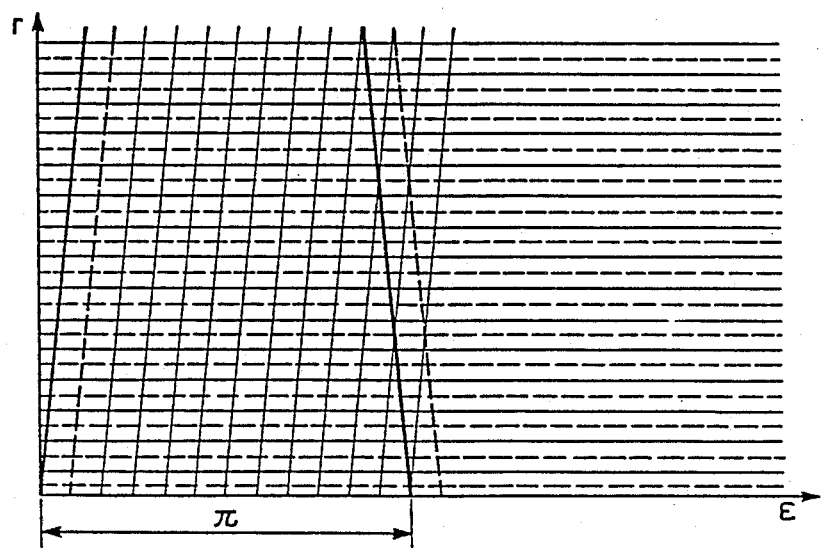

This is shown in FIG. 5. In FIG. 5, a plurality of lines which are parallel to the $\epsilon$-axis are scales of channels.

The space between the solid lines and the space between the broken lines represent the channel pitch on the positive $\theta$ side and the channel pitch on the negative $\theta$ side, respectively. When the X-ray detector is of a ¼ offset type, a deviation of ½ pitch is produced between the scale of the solid line and the scale of the broken line. On the view curve drawn from the upper right to the lower left, the point at which the view curve intersects the scale of the solid line shows the position of each channel data. On the view curve drawn from the upper left to the lower right, the point at which the view curve intersects the scale of the broken line shows the position of each channel data. If the X-ray detector is ¼ offset in the opposite direction, the scale of the solid line and the scale of the broken line are replaced by each other. When the X-ray detector is of a non-offset type, the scale of the solid line agrees with the scale of the broken line.

Figure 6:
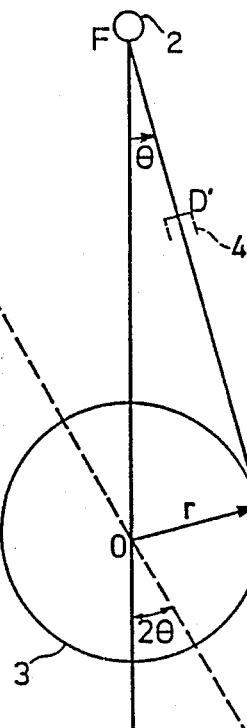

If it is assumed that it is possible to take a channel having a given designated angle, the relationship shown in FIG. 6 must be established with respect to all the channels in order to obtain the respective transmission data of the X-rays which pass the same portion of the target in the opposite directions (the data will be referred to as "opposing view data" hereinunder) by a pair of channels (hereinunder referred to as "symmetrical channels") of the X-ray detector in which the absolute values of $\theta$ are the same and the signs thereof are opposite. That is, if the data on the channel $\theta$ is taken when the X-ray source 2 is at the position F, the data on the channel $-\theta$ must be taken at the view position F' which is obtained by rotating the view position F around the center O by $\pi + 2\theta$.

For this purpose, if the pitch of the view angle (hereinunder referred to as "view pitch") is $\Delta \phi$, $$(\pi + 2\theta)/\Delta \phi$$

must be an integer, but it is difficult to satisfy the above-described condition with respect to $\theta$ of all channels under the condition that the view pitch $\Delta \phi$ is constant.

Accordingly, in the present invention, it has been taken notice of that the view position is determined by the timing for collecting channel data in the case of continuous X-rays, and complete opposing view data are collected with respect to all channels by deviating the timing for collecting data on each channel in accordance with the channel angle from the timing for collecting data in the nominal view which is determined in the direction by dividing the trajectory of the rotation of the X-ray source and the X-ray detector around the target by an equal angle $\Delta \phi$ with one point as the original point.

In other words, if the amount of deviation of timing for collecting data on one of the symmetrical channels is assumed to be $f(\theta)$, and the amount of deviation of timing for collecting data on the other channel $f(-\theta)$, the value of $$(\pi + 2\theta)/\Delta \phi + \{f(\theta) - f(-\theta)\}$$

is set at an integer. The amount of deviation of timing is determined for each view pitch.

This will be explained in more detail in the following. In the following explanation, a number m is provided for a channel of the X-ray detector. The number m is so determined that the channel on the extension of the line which connects the focal point of an X-ray and the center of the rotation of the gantry or the channel nearest thereto is 0, and starting from the channel 0, the channels on the positive side are provided with 1, 2, 3. . ., while the channels on the negative side are provide with −1, −2, −3. . .

It is assumed that the data on the channel m is collected when the X-ray source 2 is at the position F in FIG. 6, and the view angle at this timing is set at $$g(m) \cdot \Delta\phi$$

by appropriately selecting the original point of the view position. g(m) is a change in the view position due to the deviation of timing represented for each view pitch like f(θ), and it is a function of the channel number m. From the relationship of the formula (1), the following formula holds:

$$r = L \sin\{\Delta\theta(m+a)\}$$

$$\epsilon = E(m) = g(m) \cdot \Delta\phi + \Delta\theta(m+a) \quad (3)$$

wherein
L ... distance between the focal point of an X-ray and the center of the rotation of the gantry
$\Delta\phi$ ... pitch of a nominal view
$\Delta\phi$ ... channel pitch
a ... the amount of offset of the X-ray detector in each $\Delta\theta$
(in the case of an offset detector, $a = \pm\frac{1}{4}$ in the case of a non-offset detector, $a = 0$ or $\pm\frac{1}{2}$)

The amount of offset is represented by a deviation of the channel 0 from the extension of the line which connects the focal point of an X-ray and the center of rotation of the gantry, and the polarity is so set that the direction in which the channel number is positive is positive. The position of the channel is represented by the center of the channel.

$\epsilon$ of the opposite data which is to be collected by the opposing channel m' is as follows:

$$\begin{aligned}\epsilon &= \{\epsilon(m) + \epsilon(m+b)\}/2 \quad (4) \\ &= \{g(m)/2 + g(m+b)/2\}\Delta\phi + \Delta\theta(m+b/2+a)\end{aligned}$$

The value of b is 1 in the offset detector, and 0 in the non-offset detector. This is because the opposing channel m' is assumed to be situated at an intermediate position between the channel m and the channel m+1 in the offset detector, while it is assumed to be situated at the position symmetrical to the channel m in the non-offset detector.

r is as follows:

$$r = L \sin\{\Delta\theta(m+b/2+a)\} \quad (5)$$

The angle θ of the channel m' and the view angle φ are obtained from the formulas (4) and (5) as follows:

$$\begin{aligned}\theta &= -\Delta\theta(m+b/2+a) \quad (6)\\ \phi &= \epsilon - \pi - \theta \\ &= \{g(m)/2 + g(m+b)/2\}\Delta\phi + \\ &\quad 2\Delta\theta(m+b/2+a) - \pi\end{aligned}$$

The number of the channel m' for collecting the opposite data is as follows in the offset detector and the non-offset detector, respectively;
In the offset detector,
when $a = \frac{1}{4}$, $b = 1$, $m' = -(m+1)$
when $a = -\frac{1}{4}$, $b = 1$, $m' = -m$
In the non-offset detector,
when $a = 0$, $b = 0$, $m' = -m$
when $a = \frac{1}{2}$, $b = 0$, $m' = -(m+1)$
when $a = -\frac{1}{2}$, $b = 0$, $m' = -m+1$ If the view angle as that represented in the formula (6) is obtained at a position which is slightly deviated from the nominal view position which is obtained by rotating it by a multiple times the view pitch $\Delta\phi$, the view angle at this time is represented by the following formula:

$$\phi = n\Delta\phi + g(m')\Delta\phi \quad 7)$$

wherein n is an integer.
Since φ in the formula (7) is to agree with φ in the formula (6), the following relationship should hold:

$$\Delta g(m) + (2m+b+2a)\Delta\theta/\Delta\phi - n - \pi/\Delta\phi = 0 \quad (8)$$

wherein $\Delta g(m) = g(m)/2 + g(m+b)/2 - g(m')$
If the following relationship holds in the formula (8):

$$\Delta g(m) + (2m+b+2a)\Delta\theta/\Delta\phi - \pi/\Delta\phi = g \quad (9)$$

the decimal portion of g must be 0.
In the formula (9), the third term represents the number of the nominal views during a half turn of the gantry and takes a predetermined constant value, but the second term varies in accordance with the channel number m. Accordingly, in order to satisfy the above-described condition, the first term $\Delta g(m)$ should be set at a value which nullifies the decimal portion of the sum of the second term and the third term in a certain channel number m0, and the value should be varied in accordance with the variation of the second term. Since the value in the second term increases by $2\Delta\theta/\Delta\phi$ with the increase of 1 in the channel number, the amount of variation in $\Delta g(m)$ is set at $-2\Delta\theta/\Delta\phi$ so selected as to nullify the increment.

Since $\Delta g(m)$ is the difference in the deviation of the respective timings for collecting a pair of items of opposing view data, the amount of deviation of one timing and that of the other timing are allocated as desired in the range in which the difference is $2\Delta\theta/\Delta\phi$. In other words, if the allocation functions are α and β, the respective amounts of deviation may be $\alpha\Delta\theta/\Delta\phi$ and $\beta\Delta\theta/\Delta\phi$ under the condition $\alpha+\beta=2$. The direction of deviation is opposite to each other. If either of α and β is 0, only one timing is deviated without deviation of the other, and if $\alpha=\beta=1$, the amounts of deviation are the same.

Figure 7:
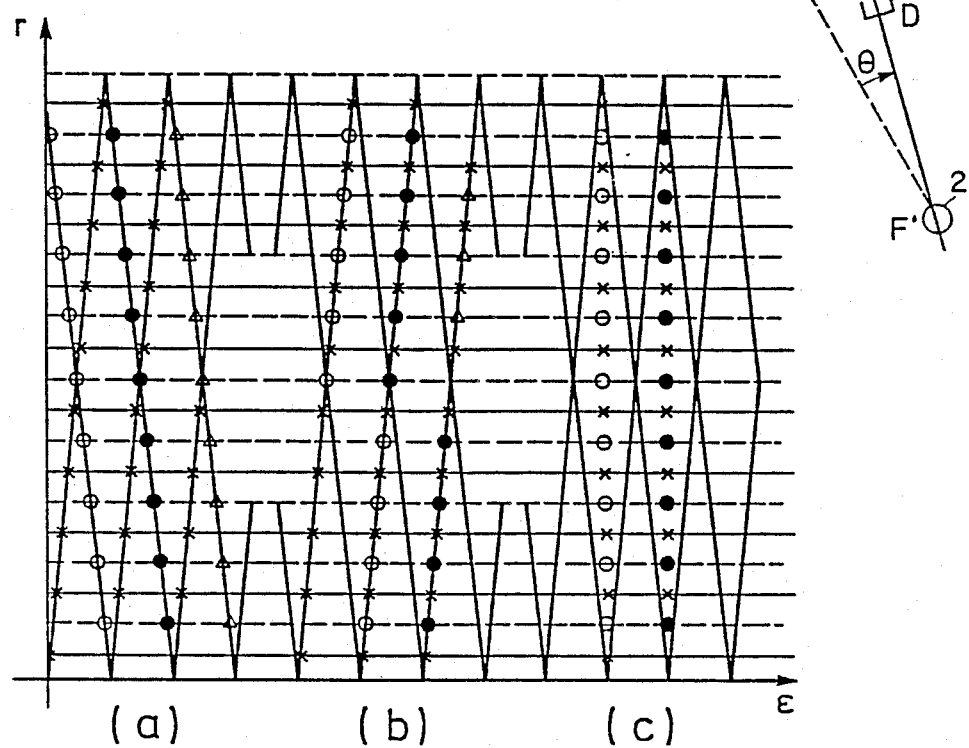

FIG. 7 shows the arrangement of data on the plane ε−r collected at the above-described timings in a $-\frac{1}{4}$ offset detector. In FIG. 7, (a) shows the arrangement of the data collected without deviation of timing for comparison with the present invention. (b) shows the arrangement of the data collected by deviating one timing. By deviating the timing for collecting the channel data on the negative θ side, these items of data are arranged on the channel data arrangement curves on the positive θ side. Thus, the opposing view data which have the data arrangement corresponding to the fan beam X-rays and which can be utilized in complete combination with each other are obtained as the real data with respect to all the channels. (c) shows the arrangement of the data collected by deviating both timings by the same amount. The channel data are arranged on the lines parallel to the r-axis between the respective original channel data arrangement curves. Thus, the opposing view data which have the data arrangement corresponding to the parallel beam X-rays and which can be utilized in complete combination with each other are obtained as the real data. Additionally, since it is sufficient in this case that the arrangement of the channel data is parallel to the r-axis, the amount of deviation of the respective timings for collecting the opposing view data may be selected from among the values obtained by varying the same value which has been set to as to have the opposite signs by a constant value.

FIG. 7 shows the case of using an offset detector, and it is obvious that in the case of using a non-offset detector complete duplex data are obtained as the real data.

The above-described channel data collection is carried out by the data collector 9 under the control of the data processor 10, and such function of the data collector 9 can be realized by an appropriate sequence control of a known electric circuit for collecting multi-channel X-ray data.

While there has been described the best mode for carrying out the present invention, it will be understood by those skilled in the art that various modifications may be made therein without departing from the scope of the following claims.

What is claimed is:

1. A method of collecting data for an X-ray tomograph in which an X-ray source for projecting continuous X-ray in the shape of fan beams and a multi-channel X-ray detector which opposes said X-ray source with an object to be examined interposed therebetween are rotated around said object to be examined, so as to project said X-rays in the shape of fan beams in a plurality of view directions in the section of said object to be examined, and reconstructing the tomogram of said object to be examined on the basis of data which indicate the distribution of the transmission intensity of said X-rays in each view direction, characterized in that the timing for collecting output data of each detection channel is so selected that the relationship in which a pair of items of data based on a pair of X-ray beams which pass a substantially common route formed in said object to be examined in opposite directions to each other are detected by a pair of channels which are situated at substantially symmetrical positions with respect to the center of said X-ray detector, is established with respect to all channels;

wherein the direction of a nominal view is set at pitch angle of $\Delta\phi$ around said X-ray detector, and
the timing for collecting each output data of said pair of channels which are situated at substantially symmetrical positions with respect to the center of said X-ray detector is deviated from the timing prescribed by said nominal view so that the difference $\Delta g(m)$ in the amount of deviation of said timing for collecting data satisfies the following relationship:

$$\Delta g(m)+(2m+b+2a)\Delta\theta/\Delta\phi-n-\pi/\Delta\phi=0$$

wherein
$\Delta\theta$ ... pitch angle of channels of said X-ray detector
m ... number of channels with the channel at the center of said X-ray detector as a reference
a ... offset of a point at which an X-ray beam which has started from said X-ray source and has passed the center of rotation enters a channel of said X-ray detector from the center of said channel
b ... when a=0 or $\pm\frac{1}{2}$, b=0, in the other case, b=1
n ... positive integer.

2. A method of collecting data for an X-ray tomograph according to claim 1, wherein the amount of deviation of timing for collecting data on one channel of said pair of channels is $\Delta g(m)$ and the amount of deviation of timing for collecting data on the other channel is zero.

3. A method of collecting data for an X-ray tomograph according to claim 1, wherein the absolute value of the amount of deviation of timing for collecting data on one channel of said pair of channels and that for collecting data on the other channel is equal and the signs thereof are opposite to each other.

* * * * *